United States Patent
Nam et al.

(10) Patent No.: US 11,747,333 B2
(45) Date of Patent: Sep. 5, 2023

(54) DETECTION METHOD OF TARGET ANALYTE USING GOLD NANOPROBE THROUGH OVERGROWTH OF COPPER CRYSTAL

(71) Applicants: SEOUL NATIONAL UNIVERSITY R&DB FOUNDATION, Seoul (KR); KOREA FOOD & DRUG ADMINISTRATION, Chungcheongbuk-do (KR)

(72) Inventors: Jwa-Min Nam, Seoul (KR); Gwangpyo Ko, Seoul (KR); Jae-Ho Kim, Seoul (KR); Jeong-Eun Park, Seoul (KR); Mouhong Lin, Seoul (KR); In Sun Joo, Chungcheongbuk-do (KR); Jeong Su Lee, Chungcheongbuk-do (KR)

(73) Assignees: KOREA FOOD & DRUG ADMINISTRATION, Chungcheongbuk-Do (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 145 days.

(21) Appl. No.: 16/486,674

(22) PCT Filed: Feb. 14, 2018

(86) PCT No.: PCT/KR2018/001956
§ 371 (c)(1),
(2) Date: Sep. 18, 2019

(87) PCT Pub. No.: WO2018/151542
PCT Pub. Date: Aug. 23, 2018

(65) Prior Publication Data
US 2020/0011864 A1 Jan. 9, 2020

(30) Foreign Application Priority Data
Feb. 16, 2017 (KR) .................. 10-2017-0021136

(51) Int. Cl.
G01N 33/553 (2006.01)
G01N 33/543 (2006.01)
(Continued)

(52) U.S. Cl.
CPC ......... *G01N 33/553* (2013.01); *G01N 33/532* (2013.01); *G01N 33/54346* (2013.01);
(Continued)

(58) Field of Classification Search
CPC ........... G01N 33/54393; G01N 33/553; G01N 33/54366; G01N 33/587; G01N 33/532;
(Continued)

(56) References Cited

U.S. PATENT DOCUMENTS 10,464,136 B2 * 11/2019 Yu .................. B22F 1/0551

FOREIGN PATENT DOCUMENTS

EP 2477031 7/2012
KR 10-2009-0087591 8/2009
(Continued)

OTHER PUBLICATIONS

Yuan et al. Sensitive and selective detection of copper ions with highly stable polyerhyleneimine-protected silver nanoclusters. Anal Chem. 2014, vol. 86, pp. 419-426 (Year: 2014).*
(Continued)

*Primary Examiner* — Shafiqul Haq
(74) *Attorney, Agent, or Firm* — Fay Kaplun & Marcin, LLP

(57) ABSTRACT

The present invention relates to a method for detecting a target analyte using a gold nanoparticle, comprising growing a copper crystal specifically on a gold nanoparticle by treating the gold nanoparticle with a solution comprising a copper ion, a polymer having a primary or secondary amine group, and a reducing agent, a composition for amplifying a signal used in the detection method above, and a kit for detecting a target analyte comprising the composition for amplifying a signal above.

15 Claims, 7 Drawing Sheets

(51) Int. Cl.
*G01N 33/532* (2006.01)
*B82Y 30/00* (2011.01)

(52) U.S. Cl.
CPC . *G01N 33/54366* (2013.01); *G01N 33/54393* (2013.01); *B82Y 30/00* (2013.01)

(58) Field of Classification Search
CPC ......... G01N 33/5306; G01N 33/54346; G01N 21/47; B82Y 30/00
See application file for complete search history.

(56) References Cited

FOREIGN PATENT DOCUMENTS

| KR | 10-2012-0053405 | 5/2012 |
|---|---|---|
| KR | 10-2013-0101289 | 9/2013 |
| KR | 10-2016-0117688 | 10/2016 |

OTHER PUBLICATIONS

Tang et al. Cost-effective aqueous-phase synthesis of long copper nanowires. RSC Adv. 2015, vol. 5, pp. 83880-83884. (Year: 2015).*
Zhang et al. Colorimetric determination of copper(I) using a polyamine-functionalized gold nanoparticle probe. Microchim Acta 2015, vol. 182, pp. 1677-1683. (Year: 2015).*
Personick et al. Making sense of the mayhem behind shape control in thesysthesis of gold nanoparticles. JACS 2013, vol. 135, pp. 18238-18247. (Year: 2013).*
Hecold et al. The effect of PEI and PVP-stabilized gold nanoparticles on quine platelets activation: potential application in equine regenerative medicine. Journal of Nanomaterials 2017, pp. 1-11 (Year: 2017).*
Yan et al., "Sensitive Naked Eye and Autofluorescence Detection of Cu2+ in Biological Fluids by Polyethyleneimine Microspheres", J Fluoresce, vol. 26, Jun. 2016, pp. 1763-1772.
Zhang et al., "Colorimetric detennination of copper(II) using a polyamine-functionalized gold nanoparticle probe", Microchim Acta, vol. 182, Apr. 2015, pp. 1677-1683.
Feng et al., "Polyethyleneimine-templated copper nanoclusters via ascorbic acid reduction approach as ferric ion sensor", Analytica Chimica Acta 853, 2015, pp. 153-160.

* cited by examiner

DETECTION METHOD OF TARGET ANALYTE USING GOLD NANOPROBE THROUGH OVERGROWTH OF COPPER CRYSTAL

TECHNICAL FIELD

The present invention relates to a method for detecting a target analyte using a gold nanoparticle, including growing a copper crystal specifically on a gold nanoparticle by treating the gold nanoparticle with a solution including a copper ion, a polymer having a primary or secondary amine group, and a reducing agent, a composition for amplifying a signal used in the detection method above, and a kit for detecting a target analyte including the composition for amplifying a signal above.

BACKGROUND ART

The development of detection methods for chemical and biological molecules with high sensitivity and high susceptibility is of great importance in realizing the potential of genetic and proteomic advances over the last decades. High-density genetic chips have enabled the simultaneous monitoring of thousands of gene expressions. In addition, lower-density genetic chips have enabled the experimental and clinical identification of potential biohazards that can occur in a single sample. Currently used labeling techniques are based on molecular fluorescent markers, but recent advances in nanoparticle technology have enabled the implementation of systems with significantly higher sensitivity and selectivity compared to conventional fluorescent-based methods.

Gold nanoparticles are not only chemically stable, but can be easily modified and exhibit excellent optical properties including plasmonic properties, and thus are widely used as probes in detecting biomaterials. However, when gold nanoparticles are used as probes, labeling with very high density and/or number is required to obtain a visible signal intensity, which indicates that the detection limits for biomaterials are fundamentally low without an additional amplification process. In order to achieve a lower detection limit, detection methods such as surface-enhanced Raman scattering (SERS), conductometric, and electrochemical stripping have been developed, but these methods have a disadvantage in that separate equipment and multi-step measurement method are needed. Thus, in order to solve the technical requirements such as point of care testing, a method for amplifying an optical scattering signal of a probe by additionally introducing silver or gold nanoshells to gold nanoparticles used for detection is used, but there are limitations in terms of reproducibility and sensitivity.

Meanwhile, although some studies that make core-shell nanoparticles by overgrowing a metal material such as copper or palladium in the form of nanoshells on colloidal gold nanoparticles have been reported, some aspects of the studies such as selectivity have not yet been reported. In addition, gold nanoparticles usually remain in the form of colloidal binary nanoparticles that do not have large size amplifications, such as thin shell-like structures.

Conventional silver enhancement method is a technology that detects biomaterials using gold nanoprobes and then reduces silver in the ion state on the surface of the gold nanoprobes to generate a strong scattering signal, and allows to determine the presence/absence of gold nanoprobes and the level thereof (high or low) without the need for an additional analyzer. However, when the silver enhancement is used, due to the inherently strong reducing nature of the silver element, silver ions are reduced even in locations where gold nanoprobes are absent, which are relatively non-specific, thereby increasing the noise signal. In addition, due to the high material cost of the precious metals, relatively high costs are required when using the silver enhancement. Thus, there is a need for a method that can easily detect a small number of gold nanoprobes with high sensitivity, selectivity and reproducibility and at low cost.

DISCLOSURE

Technical Problem

In the method of detecting a target analyte using gold nanoparticles, the present inventors have made extensive efforts to find a method that can easily and economically provide a significant signal enhancement effect in addition to a conventional method of introducing a silver shell to gold nanoparticles, which requires high cost and harsh reaction conditions, and as a result, they have found that when copper ions are reduced in the presence of a polymer having a primary or secondary amine group, the target analyte can be easily detected with high sensitivity and selectivity by overgrowing copper crystals on gold nanoparticles to several hundred nm within a few minutes at room temperature, thereby completing the present invention

Technical Solution

In one aspect to achieve the object above, the present invention provides a method for detecting a target analyte using a gold nanoparticle, including:

Step 1 of preparing a substrate on which a target analyte is immobilized directly or through a material capable of capturing the target analyte;

Step 2 of forming a complex with the target analyte by contacting a gold nanoparticle-labelled material that specifically binds to the target analyte with the substrate of Step 1; and Step 3 of growing a copper crystal specifically on the gold nanoparticle by treating the substrate, on which the complex of Step 2 is formed, with a solution including a copper ion, a polymer having a primary or secondary amine group and a reducing agent.

In another aspect, the present invention provides a composition for amplifying a signal used in the aforementioned method for detecting a target analyte using a gold nanoparticle, including a compound capable of providing a copper ion in solution, a polymer having a primary or secondary amine group, and a reducing agent.

In still another aspect, the present invention provides a kit for detecting a target analyte using a gold nanoparticle, including the aforementioned composition for amplifying a signal.

In still further another aspect, the present invention provides a method for preparing a copper crystal, including growing a copper crystal on a gold nanoparticle by treating the gold nanoparticle with a solution including a copper ion, a polymer having a primary or secondary amine group, and a reducing agent.

Hereinafter, the present invention will be described in detail.

In the method for detecting an analyte using a gold nanoparticle as a probe, the present invention is based on the findings that it is possible to grow copper nanopolyhedra of several hundred nm in size within a few minutes at room temperature without additional energy, such as heating by a simple process for treating gold nanoparticles immobilized on a substrate with a solution including a copper ion, a polymer having a primary or secondary amine group, and a reducing agent.

When copper crystals were grown on gold nanoparticles immobilized on a conventional substrate, a spatially asymmetrical environment was created around the gold nanoparticles, which had limited to diffusion-dependent growth, requiring a long time or causing inconvenience of applying energy through heating, and because of this heating process, materials such as DNA and proteins could be denatured, and thus it was difficult to apply in the detection of these materials.

Accordingly, a method of enhancing a signal by introducing a silver shell, which can be easily reduced and easily introduced, and is relatively advantageous for detection, was used, although the cost was high. As described above, it has problems in that the cost is high and non-specific silver particles are formed due to the reducing nature of the silver element, so that the selectivity is lowered and the background signal is increased together, resulting in a low signal-to-noise ratio.

The polymer having a primary or secondary amine group may be a polymer capable of forming a ligand complex with a copper ion through an amine group included therein. For example, the polymer having a primary or secondary amine group may be polyethyleneimine. The polymer having a primary or secondary amine group can be strongly bonded to copper ions through an amine group included therein to form a ligand complex, and accordingly, the chemical potential of the copper ions is reduced, thereby suppressing non-specific reduction.

The molecular weight of the polymer may be 100 to 10000, more specifically 1000 to 5000 based on the number average molecular weight or weight average molecular weight, but is not limited thereto.

As the reducing agent, for example, a mild reducing agent such as ascorbic acid, hydroxyamine or hydroquinone may be used, but is not limited thereto. By using such a mild reducing agent, it is possible to block the formation of nonspecific copper crystals and to selectively form crystals only on the gold nanoparticles, thereby improving the signal-to-noise ratio.

The solvent of the solution may be specifically water, but is not limited thereto.

Step 3 for overgrowing a copper crystal on the gold nanoparticle can be achieved by performing at room temperature, for example, 10° C. to 35° C., for 3 to 20 minutes, but is not limited thereto.

In Step 3, the particle on which the copper crystal is grown may have an increased diameter of 100 nm to 1,000 nm. The diameter may refer to the maximum diameter or the average diameter of the particle, and the maximum diameter may refer to the maximum distance between one end to the other end of the particle. Significant scattering signal enhancement can be achieved by overgrowing the copper crystal such that a particle with an increased diameter of several hundred nm can be formed as described above, and thus, it is possible to detect the target analyte with the naked eye without any additional analyzer.

By using the detection method of the present invention, the presence and absence of the target analyte or the level thereof (high or low) can be confirmed by the naked eye or a microscope, or by taking images using photography.

Further, quantitative analysis is also possible when analyzing intensity histograms derived from images of photographs, or when using a scanner.

As described above, the specific overgrowth of a copper crystal on a gold nanoparticle according to the invention may provide a detection method capable of improving a signal-to-noise ratio up to several tens to tens of thousands, as compared to conventional detection methods, because copper hardly forms crystals in the absence of gold nanoparticles, unlike silver which forms particles, due to its reducing nature, even in the locations where gold nanoparticles that can act as seeds are absent, i.e., in the locations where gold nanoparticles are absent due to the absence of a target analyte. For example, the signal-to-noise ratio that can be achieved by the detection method of the present invention may vary depending on the concentration of the target analyte, and may be 20 to 100 for 8 fM gold nanoprobes, but is not limited thereto. For example, in the case of a conventional detection method using silver instead of copper, which is similar to the detection method of the present invention, the signal of the gold nanoprobe itself as well as the background signal increases due to the formation of non-specific silver crystals, so that it was difficult to improve the signal-to-noise ratio. However, the detection method using the overgrowth of copper crystals according to the present invention can significantly improve the signal-to-noise ratio because copper crystals are selectively formed only where gold nanoprobes are present.

The signal-to-noise ratio may refer to the ratio of the signal when the gold nanoprobe is added to the background signal when the gold nanoprobe is not added.

Specifically, considering that the signal-to-noise ratio can be regarded as a significant signal when the ratio is 2 to 5 or more, the detection method using copper according to the present invention showed a signal-to-noise ratio of at least 20 for 8 fM gold nanoprobes. In contrast, the signal-to-noise ratio was only about 1 when silver was used. These results indicate that even a trace amount of target analytes present at a concentration below fM can be detected based on the significantly improved signal-to-noise ratio.

The method for detecting a target analyte using gold nanoparticles of the present invention may be performed using a composition for amplifying a signal including a compound capable of providing a copper ion in solution, a polymer having a primary or secondary amine group, and a reducing agent.

For example, the compound capable of providing a copper ion in solution may be copper chloride, but is not limited thereto.

For example, the polymer having a primary or secondary amine group is a polymer capable of forming a ligand complex with a copper ion. Specifically, the polymer having the primary or secondary amine group may be polyethyleneimine, but is not limited thereto.

In addition, non-limiting examples of the reducing agent that can be used in the composition for amplifying a signal of the present invention include ascorbic acid, hydroxylamine or hydroquinone.

Further, the present invention may provide a kit for detecting a target analyte using a gold nanoparticle including the aforementioned composition for amplifying a signal.

Herein, the kit may further include, but is not limited to, a solution containing water as a solvent.

For example, the kit for detecting a target analyte of the present invention may be advantageously used for signal amplification of gold nanoparticles which are directly and indirectly immobilized to a substrate through a specific binding with a target analyte.

In addition, the present invention may provide a method for preparing a copper crystal, including growing a copper crystal on a gold nanoparticle by treating the gold nanoparticle with a solution including a copper ion, a polymer having a primary or secondary amine group, and a reducing agent.

Advantageous Effects

The method for detecting a target analyte using a gold nanoparticle, including growing a copper crystal on a gold nanoparticle by treating the gold nanoparticle with a solution including a copper ion, a polymer having a primary or secondary amine group, and a reducing agent of the present invention can grow a copper crystal selectively on a gold nanoparticle to several hundred nm within a few minutes at room temperature and can detect a target analyte with an excellent signal-to-noise ratio without the need of a separate analyzer, and thus can be effectively used in the detection of trace amount of a target analyte.

DETAILED DESCRIPTION OF EMBODIMENTS

The present invention will be described in more detail through exemplary embodiments. However, these exemplary embodiments are provided for illustrative purposes only, and are not intended to limit the scope of the invention.

Preparation Example 1: Synthesis of Gold Nanoprobe Labeled with Gold Nanoparticles on Antibodies for Norovirus Detection Gold nanoparticles (1 mL) having a diameter of 50 nm dispersed in distilled water were reacted with polyethylene glycol (PEG) polymers (MW 5K, 200 μM, 0.1 mL) having each of a thiol group (—SH) and a carboxyl group (—COOH) at both ends for 3 hours at room temperature to allow PEG polymers to bind to the surface of gold nanoparticles through a thiol group. The supernatant was removed by centrifugation at 6000 rpm for 10 minutes, then suspended in 0.25 mL of 50 mM MES buffer (2-(N-orpholino) ethanesulfonic acid, pH 4.8) and allowed to react with 0.1 mL of 1-Ethyl-3-(3-dimethylaminopropyecarbodiimide (EDC) at a concentration of 1 mg/mL and 0.1 mL of N-hydroxysulfosuccinimide (sulfo-NHS) at a concentration of 0.1 mg/mL at room temperature for 5 minutes to activate the carboxyl group. Again, the supernatant was removed by centrifugation at 6500 rpm for 15 minutes, suspended in 0.25 mL of 10 mM PBS (phosphate buffered saline, pH 7.2) and reacted with an anti-norovirus capsid protein VP1 antibody (Abcam, UK, #ab92976) at pH 7.2 for 3 hours at room temperature to allow the PEG-modified gold nanoparticles to bind through the amine group of the antibody using the activated carboxyl group. After repeating centrifugation twice at 6500 rpm at 4° C. for 10 minutes, the supernatant was removed and suspended in 0.05% PBST (phosphate buffered saline with Tween-20) to obtain a gold nanoprobe solution having a concentration of 200 pM.

Figure 4:
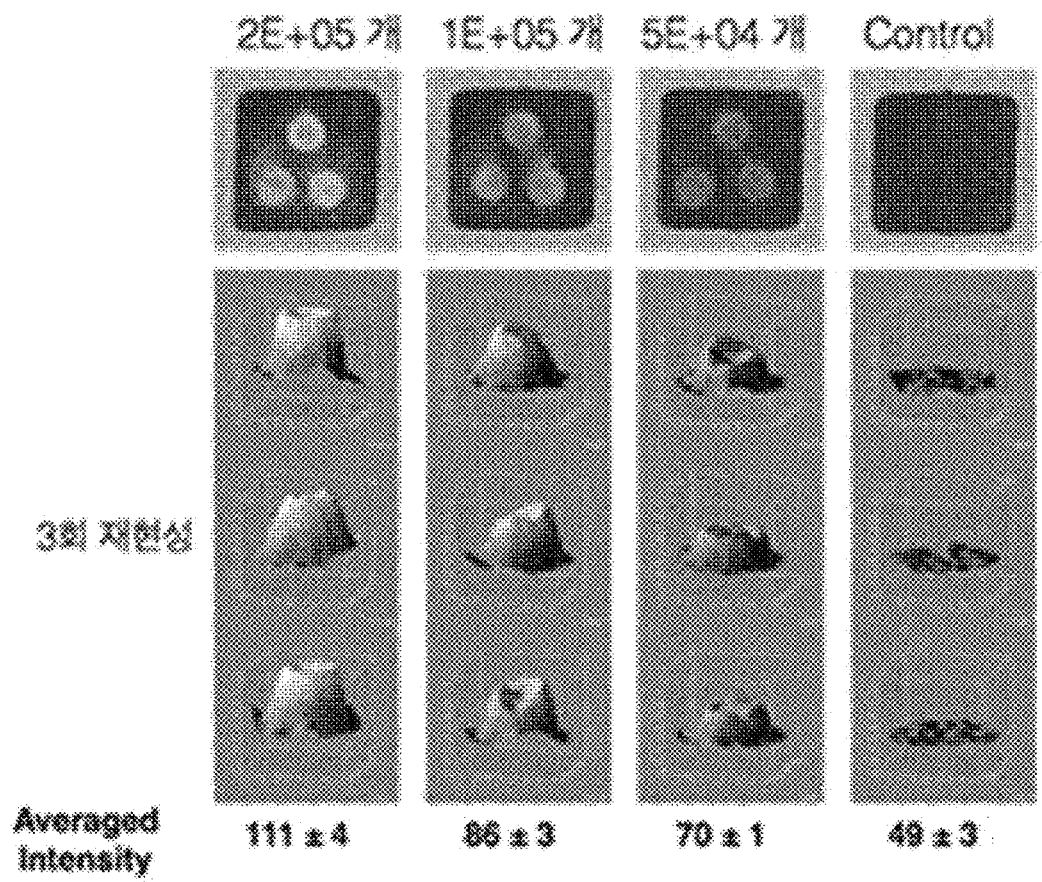
FIG. 4 is a diagram showing the results of norovirus detection using specific copper crystal overgrowth on the gold nanoprobes according to the present invention.
Figure 4:
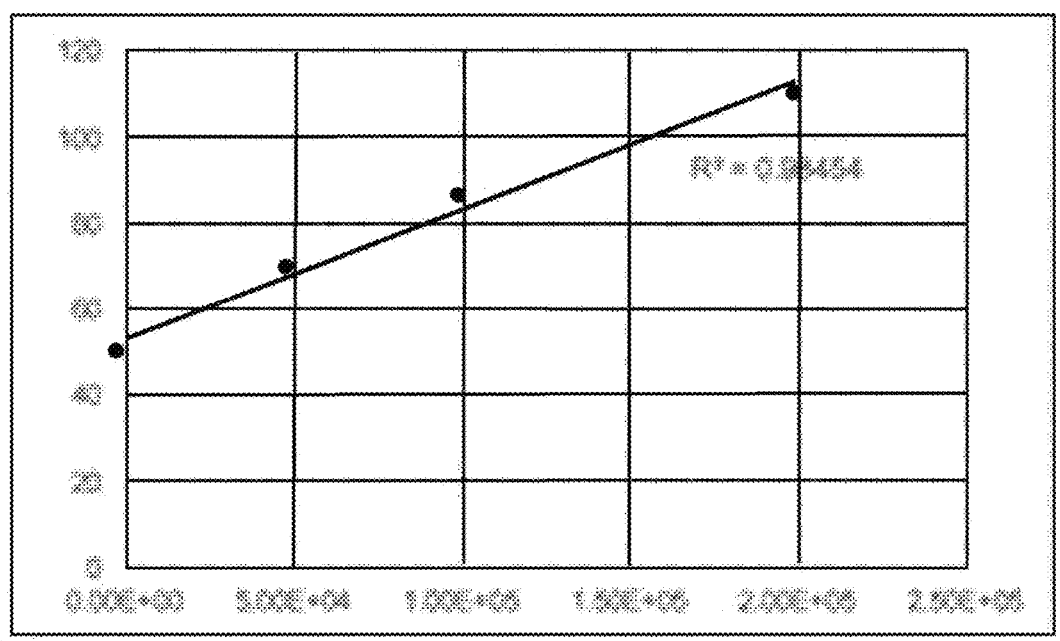
Figure 5:
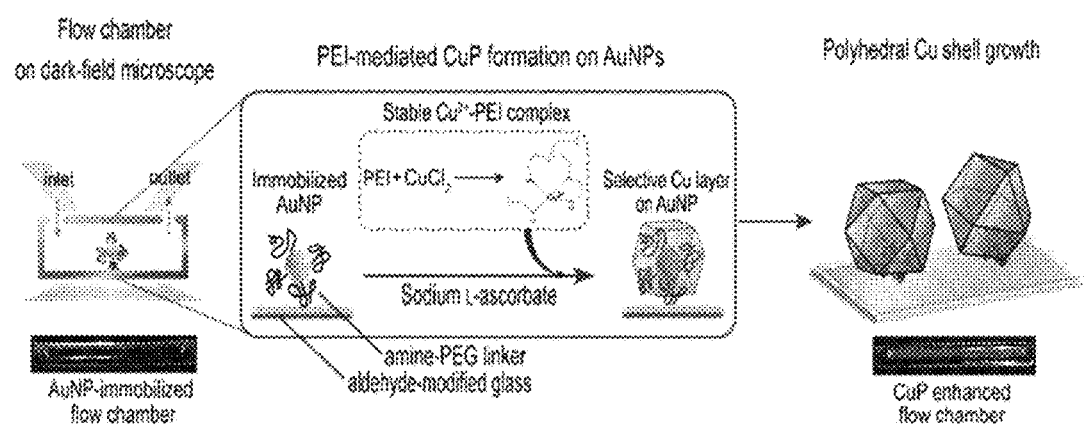
FIG. 5 is a diagram showing specific overgrowth of a copper crystal by a polymer having primary or secondary amine groups on a gold nanoparticle according to the present invention.
Figure 6:
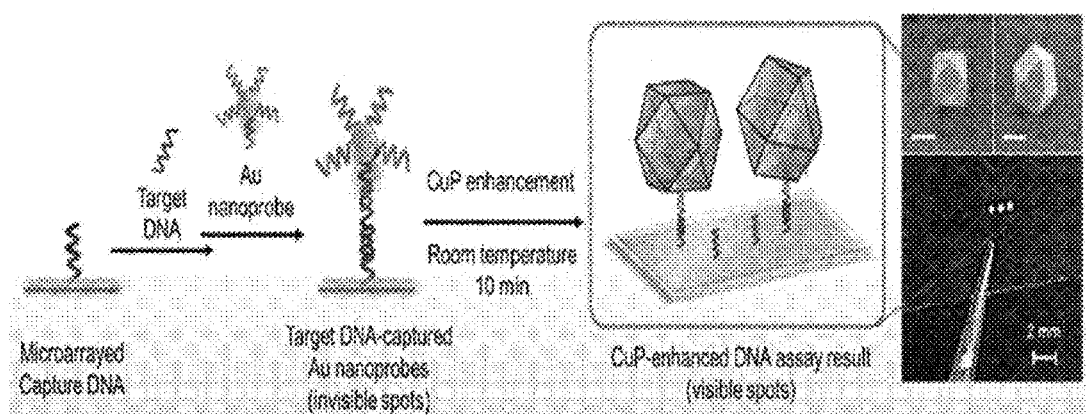
FIG. 6 is a diagram illustrating a DNA detection method using copper crystal overgrowth according to the present invention.
Figure 7:
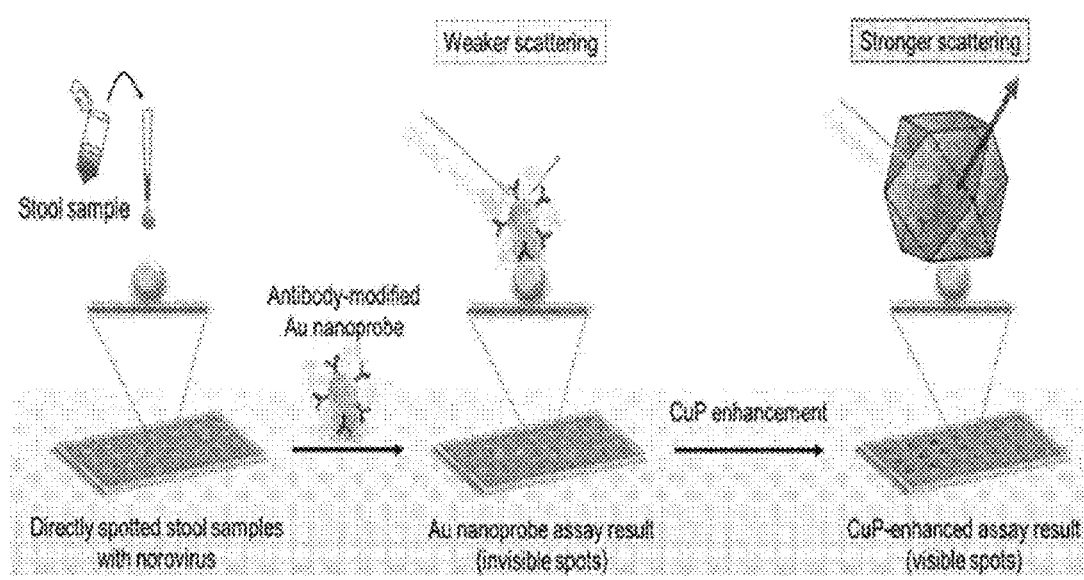
FIG. 7 is a diagram showing a norovirus detection method using copper crystal overgrowth according to the present invention.

Example 1: Norovirus Detection Method Using Gold Nanoparticle-Specific Copper Crystal Overgrowth 1 μL of a solution prepared by mixing a virus sample and 10 mM Tris buffer in a 1:1 volume ratio was loaded onto an aldehyde-modified glass substrate (Aldehyde glass, Luminano) and reacted at room temperature for 2 hours to allow the virus sample to bind to the glass substrate. After washing the glass substrate three times with 2 mL of 0.05% PBST, the exposed surface was blocked by treatment with 1% BSA solution for 30 minutes at room temperature. After washing the glass substrate three times with 2 mL of 0.05% PBST, 8 μL of the gold nanoprobe solution prepared according to Preparation Example 1 was added thereto, and allowed to react at room temperature for 1 hour and washed three times with 2 mL of 0.05% PBST. Then, the glass substrate in which the reaction was completed was soaked into 35 mL of a copper enhancer solution prepared by mixing 5 mL of 0.1 M copper chloride (CuCl2), 5 mL of 1% polyethyleneimine (PEI), and 25 mL of 0.5 M ascorbic acid and allowed to react at room temperature for 10 minutes to overgrow the copper crystals on the gold nanoprobe. After the reaction was completed, the glass substrate was washed with water and dried. The substrate, on which the copper crystals were overgrown, was analyzed by ImageJ software to quantify the signal values, and the results are shown in FIG. 4.

Preparation Example 2: Synthesis of Gold Nanoprobe Labeled with Gold Nanoparticles on DNA for Detection of *Bacillus anthracis* Gene 5'-end thiolated *Bacillus anthracis* probe oligonucleotides (SEQ ID NO: 1: 5'-SH-$A_{10}$-$PEG_{18}$-AAT GCT TTA TTC CAT TCC TGA TTT ATA TTT AAC TGT GCT T-3') was added in excess into a 10 nm diameter-gold nanoparticle solution at a concentration of 10 nM. The salt concentration was gradually increased to reach a final concentration of 0.15 M by adding 2.0 M NaCl solution using a double boiler containing hot water (95° C.). After centrifugation at 17000 rpm for 40 minutes, the supernatant was removed and suspended in 0.5 mL of 0.1% SDS, 1×PBS to prepare a DNA-modified gold nanoparticle solution at a concentration of 500 pM, which was then used as a gold nanoprobe.

Example 2: Detection of *Bacillus anthracis* Gene Using Gold Nanoparticle-Specific Copper Crystal Overgrowth Capturing oligonucleotides (SEQ ID NO: 2: 5'-CTT GAA TTT TTG TAT CTA TTT TAC TCT TTG GCA CTA CTT T-PEG$_{18}$-C$_6$ Amine-3') were diluted to 5 µM with carbonate buffer at pH 10 containing 0.15 M NaCl, 0.01% SDS and 5% glycerol. Using a microarray, the capturing oligonucleotide solution was directly spotted with a diameter of about 500 µm on an aldehyde-modified glass substrate and allowed to stay overnight. The substrate spotted with the capturing oligonucleotide solution was washed with 0.1% SDS, 1×PBS. A silicon chamber for hybridization was attached to the thus-washed substrate. 20 µL of a target oligonucleotide solution (SEQ ID NO: 3: 5'-AAA GTA GTG CCA AAG AGT AAA ATA GAT ACA AAA ATT CAA GAA GCA CAG TTA AAT ATA AAT CAG GAA TGG AAT AAA GCA TT-3') dissolved in 0.1% SDS, 1×PBS was added thereto at concentrations of 800 fM, 80 fM, and 8 fM. Then, the substrate was hybridized by incubating for 2 hours in a wet environment of 30° C. When the reaction was completed, the substrate was washed with 0.1% SDS, 1×PBS and added with 18 µL of a gold nanoprobe solution containing 500 pM probe oligonucleotides prepared according to Preparation Example 2. Then, the substrate was hybridized by incubating for 1 hour 30 minutes in a wet environment of 30° C. and washed three times with 0.1% SDS, 1×PBS. After further washing with 1×PBS, the copper enhancer solution prepared in Example 1 was added thereto and allowed to react for 5 minutes at room temperature to grow copper crystals. After the reaction was completed, the substrate was washed with water and dried.

Comparative Example 1: Nonspecific Growth of Copper Crystals on Substrate Not Containing Gold Nanoprobe A copper enhancer solution was added to the substrate treated in the same manner as in Example 1 or 2 and allowed to react for 30 minutes to confirm the formation of copper crystals, except that the gold nanoprobe solution was not added (see right side of FIG. 3).

Comparative Example 2: DNA Detection Using Silver Crystal Growth

Figure 1:
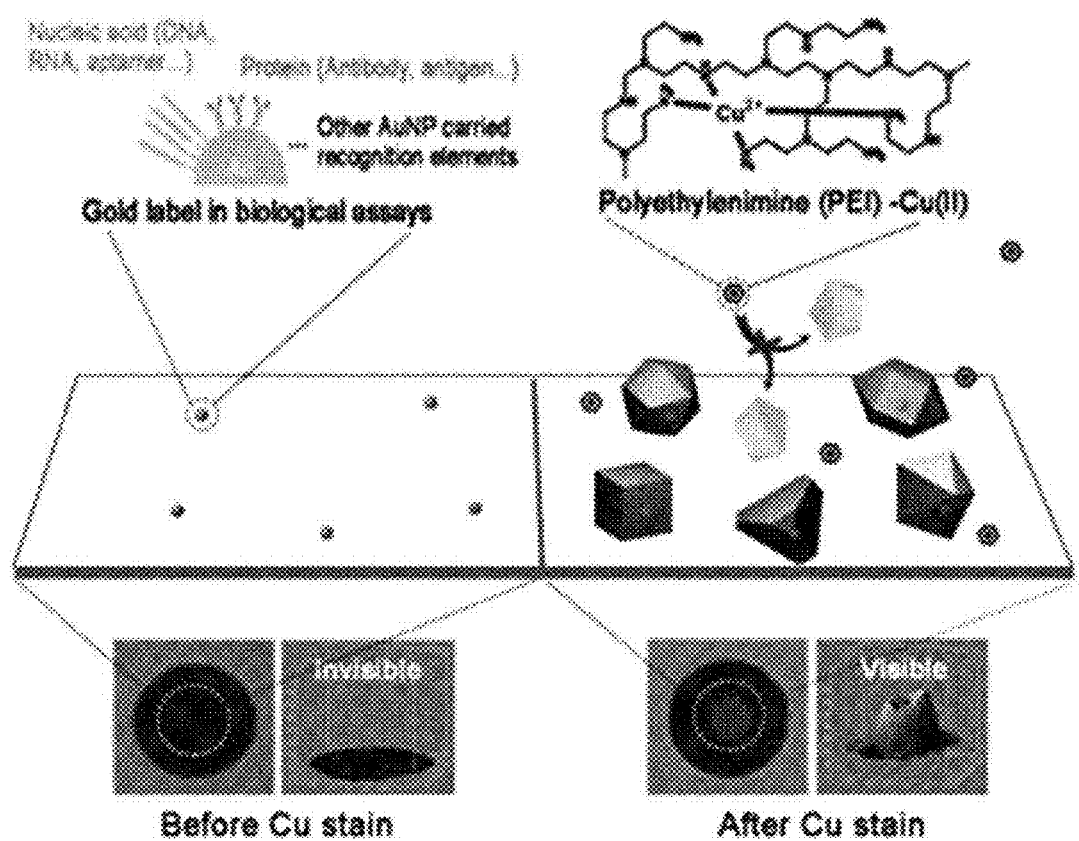
FIG. 1 is a schematic representation of specific copper crystal overgrowth on gold nanoprobes according to the present invention.
Figure 2:
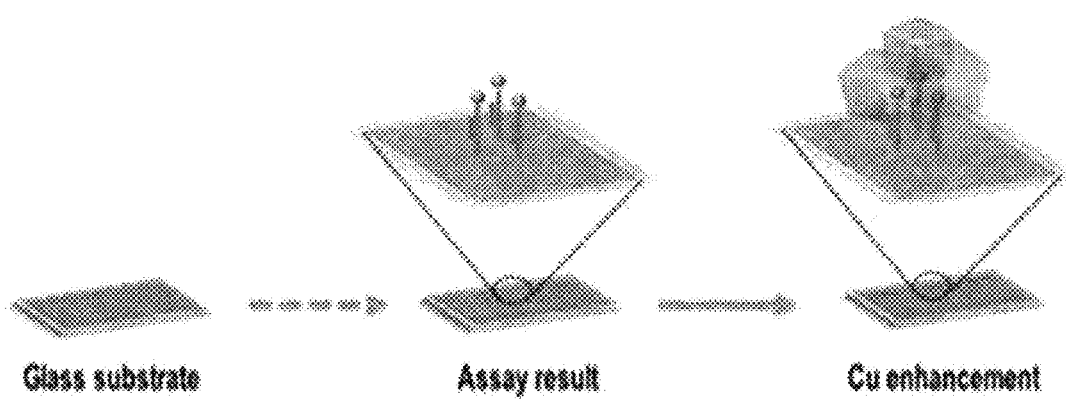
FIG. 2 is a schematic representation of a method for detecting an analyte labeled with gold nanoprobes using copper crystal overgrowth.
Figure 3:
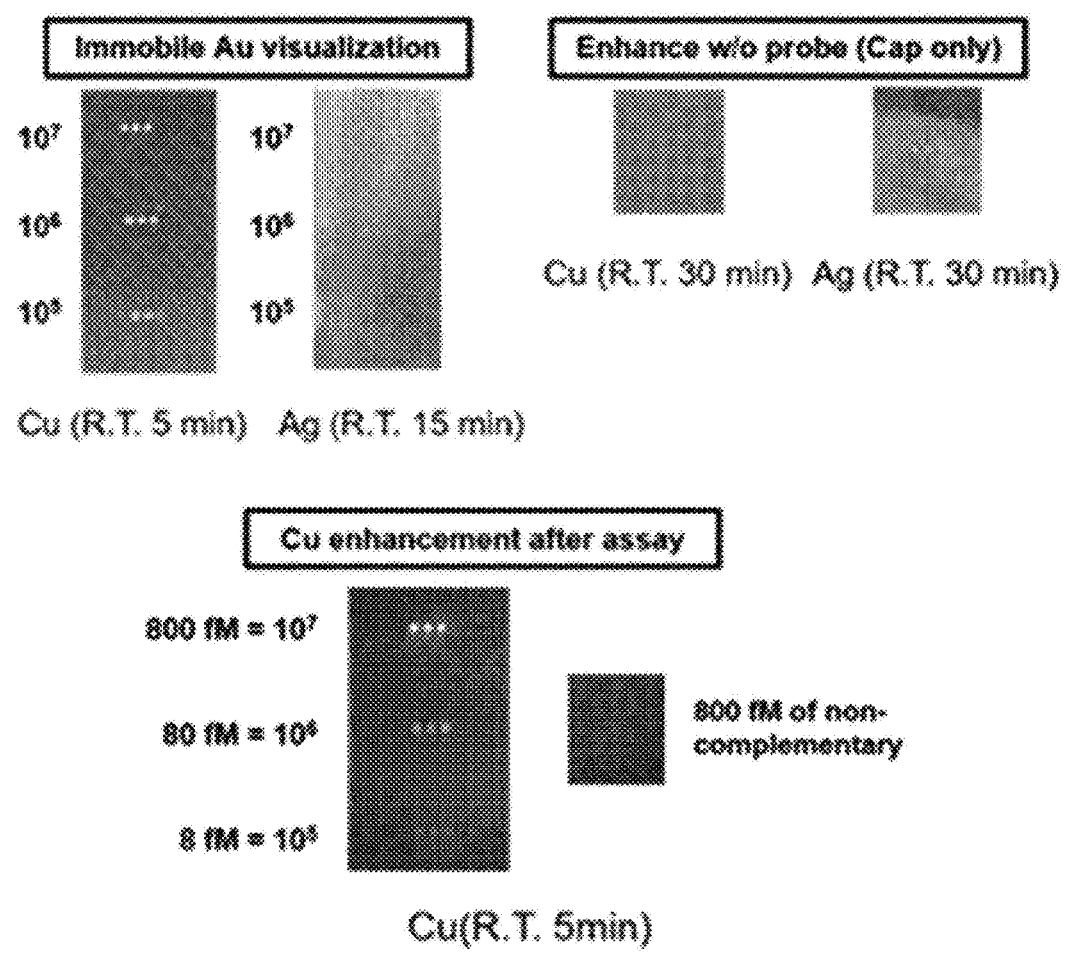
FIG. 3 is a diagram showing DNA detection results using the number of gold nanoprobes and specific copper crystal overgrowth on the gold nanoprobes according to the present invention. As the control, the analysis result using silver instead of copper was used.

The substrates with or without gold nano probe according to Examples 1 and 2, and Comparative Example 1 were incubated with a silver enhancer solution (SE100—Silver Enhancer Kit) manufactured by Sigma-Aldrich for 15 minutes (Examples 1 and 2) or 30 minutes (Comparative Example 1), and washed to observe formed silver crystals. As a result, as shown in FIG. 3, when the copper crystals were grown by treating the gold nanoprobes introduced on the substrate with a copper enhancer solution, a significant signal enhancement effect was observed compared to the case where the silver crystals were formed, thereby confirming that the target analytes could be detected at lower concentrations (left side of FIG. 3). Further, when no gold nanoprobe was included, no signal was detected in the substrate treated with the copper enhancer solution. In other words, it was confirmed that no copper crystals were formed when no gold nanoprobe was present, however, a signal was detected in the substrate treated with the silver enhancer solution (right side of FIG. 3). These results indicate that silver nanoparticles are formed nonspecifically even in the absence of gold nanoprobe serving as a seed when treated with the silver enhancer solution, and also that specific crystal growth is only possible in the presence of gold nanoprobe when treated with the copper enhancer solution, resulting in higher selectivity for analysis (center of FIG. 3).

Experimental Example 1: Reproducibility for Repeated Experiments

Substrates reacted with samples each containing 5×, 10×, and 20×10$^4$ noroviruses according to Example 1 were treated with gold nanoprobes labeled with an anti-norovirus capsid protein VP1 antibody. A copper enhancer solution was added to the substrates, on which the gold nanoprobes were immobilized, and incubated for 10 minutes to grow copper crystals. Subsequently, the substrates were washed, and the thus-formed copper crystals were visually observed and photographed for analysis. The experiment was repeated three times each and the measured signals were digitized to derive the means and standard deviations. As a result, as shown in FIG. 4, the detection method using the gold nanoprobes through the copper enhancement according to the present invention showed excellent reproducibility in the repeated experiments, and further, it was confirmed that the measured signals were proportionally increased according to the concentration of the gold nanoprobes bonded to the analytes.

SEQUENCE LISTING

1; DNA; thiolated-probe oligonucleotide; 5'-SH-A$_{10}$-PEG$_{18}$-AAT GCT TTA TTC CAT TCC TGA TTT ATA TTT AAC TGT GCT T-3'; 50 nucleotides 2; DNA; capturing oligonucleotide; 5'-CTT GAA TTT TTG TAT CTA TTT TAC TCT TTG GCA CTA CTT T-PEG$_{18}$-C$_6$ Amine-3'; 40 nucleotides 3; DNA; target oligonucleotide; 5'-AAA GTA GTG CCA AAG AGT AAA ATA GAT ACA AAA ATT CAA GAA GCA CAG TTA AAT ATA AAT CAG GAA TGG AAT AAA GCA TT-3; 80 nucleotides

The invention claimed is:

1. A composition for amplifying an optical scattering signal from a biological material labelled with a gold nanoparticle, the optical scattering signal generated in response to a light delivered to the biological material, the composition comprising:
   a copper ion in solution;
   a polymer comprising a primary or a secondary amine group, the primary or the secondary amine group reacts with the copper ion, wherein said polymer comprising a primary or a secondary amine group is polyethyleneimine;
   a reducing agent, wherein said reducing agent is ascorbic acid, hydroxylamine or hydroquinone; and
   the gold nanoparticle,
   wherein a copper crystal is specifically presented on a surface of the gold nanoparticle, and said copper crystal is formed by a reaction of the copper ion and the polymer comprising a primary or a secondary amine group and the reducing agent.

2. The composition of claim 1, wherein the primary or the secondary amine group reacts with the copper ion to form a ligand complex.

3. The composition of claim 1, wherein the copper ion is provided from CuCl$_2$.

4. The composition of claim 1, wherein the biological material is a target analyte.

5. The composition of claim 4, wherein the biological material is an assay reagent configured to bind to the target analyte.

6. The composition of claim 5, wherein the assay reagent is an antibody or an oligonucleotide.

7. The composition of claim 1, wherein, upon contact with the nanoparticle, the composition foinis a shell structure on the gold nanoparticle.

8. The composition of claim 7, wherein, upon contact with the gold nanoparticle, the composition forms the shell structure on the gold nanoparticle without application of additional energy.

9. The composition of claim 7, wherein, upon contact with the gold nanoparticle, the composition forms the shell structure on the gold nanoparticle at room temperature.

10. The composition of claim 7, wherein, upon contact with the gold nanoparticle, the composition forms the shell structure on the gold nanoparticle at a temperature from 10° C. to 35° C. in 3 to 20 minutes.

11. The composition of claim 7, wherein formation of the shell structure onto the gold nanoparticle increases the optical scattering signal from the labelled material.

12. The composition of claim 11, wherein the formation of the shell structure onto the gold nanoparticle increases a signal-to-noise ratio for detection of the labelled material to at least 5.

13. The composition of claim 12, wherein the signal-to-noise ratio is at least 20.

14. The composition of claim 1, wherein the gold nanoparticle has a diameter of 50 nm.

15. The composition of claim 7, wherein the shell structure has an external diameter of 100 nm to 1,000 nm.

* * * * *